(12) United States Patent
Kerrigan et al.

(10) Patent No.: US 9,648,812 B2
(45) Date of Patent: May 16, 2017

(54) MUSHROOM LINE J10102-S69 AND METHODS AND USES THEREFOR

(71) Applicant: Sylvan America, Inc., Kittaning, PA (US)

(72) Inventors: Richard W. Kerrigan, Kittaning, PA (US); Mark P. Wach, Allison Park, PA (US); Michelle E. Schultz, New Bethlehem, PA (US)

(73) Assignee: Sylvan America, Inc., Kittaning, PA (US)

( * ) Notice: Subject to any disclaimer, the term of this patent is extended or adjusted under 35 U.S.C. 154(b) by 493 days.

(21) Appl. No.: 14/169,578

(22) Filed: Jan. 31, 2014

(65) Prior Publication Data

US 2015/0216127 A1 Aug. 6, 2015

(51) Int. Cl.
*A01H 15/00* (2006.01)
*A01H 1/02* (2006.01)
*C12R 1/645* (2006.01)
*A01H 1/04* (2006.01)

(52) U.S. Cl.
CPC .................. *A01H 1/02* (2013.01); *A01H 1/04* (2013.01); *A01H 15/00* (2013.01); *C12R 1/645* (2013.01)

(58) Field of Classification Search
None
See application file for complete search history.

(56) References Cited

PUBLICATIONS

Hintz et al 1985 Current Genetics 9: 127-132.*
Morin et al 2012, PNAS Early Edition.
Velco, A.J. Jr., Kerrigan, R.W., MacDonald, L.A. Wach, M.P., Schlagnhaufer, C., and Romaine, C.P. 2004, Expression of novel genes in Agaricus bisporus using an Agrobacterium.

* cited by examiner

*Primary Examiner* — David H Kruse
(74) *Attorney, Agent, or Firm* — Renner Kenner, Greive Bobak, Taylor & Weber

(57) ABSTRACT

A culture comprising at least one set of the chromosomes of the *Agaricus bisporus* line J10102-s69, the culture of the line J10102-s69 having been deposited under the NRRL Accession Number 50893, wherein said chromosomes comprise all of the alleles of the line J10102-s69 at the sequence-characterized marker loci listed in Table I. Methods are provided for introducing a desired trait into a culture of *Agaricus bisporus* line J10102-s69, as well as methods and processes for producing hybrid mushroom cultures. A method of mushroom strain development is further provided.

27 Claims, No Drawings

US 9,648,812 B2

MUSHROOM LINE J10102-S69 AND METHODS AND USES THEREFOR

TECHNICAL FIELD

This invention relates generally to the field of microorganism strain development and more particularly, to the development of a homokaryotic line of mushroom fungus. More specifically, the present invention relates to the development of a homokaryotic *Agaricus bisporus* mushroom fungus line culture designated J10102-s69 and to cultures descended, or otherwise derived, from line J10102-s69.

BACKGROUND OF THE INVENTION

The edible mushroom *Agaricus bisporus* (Lange) Imbach var. *bisporus*, a microorganism belonging to the basidiomycete fungi, is widely cultivated around the world. Accordingly, development of novel hybrid mushroom strains or lines of this mushroom fungus is seen as highly desirable to the cultivated mushroom industry, particularly if those novel strains or lines can be developed to provide various desirable traits within a single strain, culture, hybrid or line.

Thus, various entities within the mushroom industry, including Sylvan America, Inc., have set up mushroom strain development programs. The goal of a mushroom strain development program is to combine, in a single strain, culture, hybrid, or line, various desirable traits. Strains currently available to the mushroom industry allow growers to produce crops of mushrooms successfully and profitably. Several factors exist that influence the degree of success and profitability achieved. Characteristics of strains that are factors that can improve producer profitability include increased productivity (higher yield or shorter cycle time), accelerated revenue capture (earlier harvest), reduced costs (for example, greater ease and speed of harvesting), reduced shrinkage (pre-sale weight loss), reduced overweighting of product in packages (extra weight of product packaged, due to particular sizes of individual mushrooms), improved consistency of crop performance responses to variations in raw materials, growing conditions and practices, superior crop performance in particular facilities, regions, etc., reduced losses to diseases including viral, bacterial and fungal disease agents, and/or reduced losses to insect and nematode pests of the crop. There also exist improvable properties of the mushroom product that increase demand in the distribution chain, and thus sales volume and/or sales price, such as improved visual appeal (more desirable coloration, shape, size, or surface texture), improved or distinct flavor characteristics, improved keeping qualities (longer persistence of desirable visual attributes), etc. Still other improvements may enhance the suitability of the mushroom crop for mechanical harvesting, canning, and/or food processing. Thus there are many characteristics by which a novel strain might be judged as superior in a particular production facility or sales market, or in the industry regionally or globally. All of these characteristics can be assessed using techniques that are well known in the art. Novel strains are most preferably and successfully developed from unique hybridizations between homokaryotic lines, including novel lines. Thus, the need continues to exist for new lines that can be used to produce new hybrid strains of *Agaricus bisporus* mushroom cultures and microorganisms that provide improved characteristics for producer profitability and for improved mushroom products over other previous strains of *Agaricus bisporus*.

There is also a need for commercially acceptable *A. bisporus* strains with different genotypes, relative to the U1 derived lineage group, for two reasons. First, strains incompatible with strains of the U1 derived lineage group are known to retard the spread of viral diseases between cultivated strains. The incompatibility phenotype can be assessed using techniques that are well known in the art. Second, it is well understood that when an agricultural crop industry relies extensively on a single genetic lineage (i.e., creates a commercial monoculture as now exists for the white-capped U1 lineage of *A. bisporus*), there is an increased risk of unpredictable, catastrophic crop failure on a facility-wide or even industry-wide scale. Therefore from a risk management and food security perspective, it is highly desirable to simultaneously provide both genetic diversification and commercially acceptable performance and crop characteristics. The use of novel lines that incorporate DNA from non-cultivar stocks provides important genetic diversification of the strain pool used to produce crops of cultivated *A. bisporus* mushrooms.

Cultures are the means by which the mushroom strain developers prepare, maintain, and propagate their microorganisms. Cultures of *Agaricus*, like those of other microorganisms, are prepared, maintained, propagated and stored on sterile media using various microbiological laboratory methods and techniques. Sterile tools and aseptic techniques are used within clean rooms or sterile transfer hoods to manipulate cells of pure cultures for various purposes including clonal propagation and for the development of new strains using diverse techniques. Commercial culture inocula including mushroom 'spawn' and 'casing inoculum' are also prepared using large-scale microbiological production methods, and are provided to the end user as pure cultures contained within sterile packaging.

One use of such cultures is to produce mushrooms. Mushrooms are cultivated commercially within purpose-built structures on dedicated farms. While there are many variations on methods, the following description is typical. Compost prepared from lignocellulosic material such as straw, augmented with nitrogenous material, is finished and pasteurized within a suitable facility. Mushroom spawn, which comprises a sterilized friable 'carrier substrate' onto which a pure culture of one mushroom strain has been aseptically incorporated via inoculum and then propagated, is mixed with the pasteurized compost and is incubated for approximately 13 to about 19 days at a controlled temperature, during which time the mycelium of the mushroom culture colonizes the entire mass of compost and begins to digest it. A non-nutritive 'casing layer' of material such as peat is then placed over the compost to a depth of from about 1.5 to about 2 inches. Additional 'casing inoculum' incorporating the same mushroom culture may be incorporated into the casing layer to accelerate the formation and harvesting of mushrooms, and improve uniformity of the distribution of mycelium and mushrooms in and on the casing surface. Environmental conditions, including temperature and humidity, in the cropping facility are then carefully managed to promote and control the transition of the culture from vegetative to reproductive growth at the casing/air interface. In a further about 13 to about 18 days after casing, mushrooms will have developed to the correct stage for harvest and sale. A flush of mushrooms comprising the original culture will be picked over a 3 to 4 day period. Additional flushes of mushrooms appear at about weekly intervals. Commercially, two or three flushes of mushrooms are produced and harvested before the compost is removed and replaced in the cropping facility.

*Agaricus bisporus* has a reproductive syndrome known as amphithallism, in which two distinct life cycles operate concurrently. As in other fungi, the reproductive propagule is a spore. *Agaricus* produces spores meiotically, on a meiosporangium known as a basidium. In a first life cycle, *A. bisporus* spores each receive a single haploid postmeiotic nucleus; these spores are competent to mate but not competent to produce mushrooms. These haploid spores germinate to produce homokaryotic offspring or lines which can mate with other compatible homokaryons to produce novel hybrid heterokaryons that are competent to produce mushrooms. Heterokaryons generally exhibit much less ability to mate than do homokaryons. This lifecycle is called heteromixis, or more commonly, outbreeding. This life cycle operates but typically does not predominate in strains of *Agaricus bisporus* var. *bisporus*.

A second, inbreeding life cycle called intramixis predominates in most strains of *Agaricus bisporus* var. *bisporus*. Most spores receive two post-meiotic nuclei, and most such pairs of nuclei consist of Non-Sister Nuclear Pairs (NSNPs) which have a heteroallelic genotype at most or all centromeric-linked loci including the MAT locus. That MAT genotype determines the heterokaryotic phenotype of these offspring, which are reproductively competent and can produce a crop of mushrooms. Unusually among eukaryotes, relatively little chromosomal crossing-over is observed to have occurred in postmeiotic offspring of *Agaricus bisporus*; empirically, very little heteroallelism (analogous to heterozygosity) is lost among heterokaryotic offspring of a heterokaryotic strain. Consequently, parental and offspring heterokaryotic genotypes and phenotypes tend to closely resemble each other, as noted above. For this reason, essential derivation, e.g., the production of Essentially Derived Varieties (EDVs), is a familiar strain development technique among commercial mushroom spawn producers.

Therefore, the need exists for the development of new *Agaricus bisporus* lines that meet the needs and desires of mushroom producers, marketers and consumers.

SUMMARY OF THE INVENTION

The present invention is directed generally to a new and distinct homokaryotic line of *Agaricus bisporus* designated J10102-s69, and processes for using the line designated J10102-s69. A deposit of a culture of the *Agaricus bisporus* line J10102-s69, as disclosed herein, has been made with the Agricultural Research Services Culture Collection (NRRL) 1815 North University Street, Peoria, Ill. 61604 USA. The date of deposit was Jan. 15, 2014. The culture deposited was taken from the same culture maintained by Sylvan America, Inc., Kittanning, Pa., USA, the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50893. The deposit will be maintained in the depository for a period of 30 years, or 5 years after the last request, or for the effective life of the patent, whichever is longer, and will be replaced as necessary during that period. The culture will be irrevocably and without restriction or condition released to the public upon the filing of the patent application or upon the issuance of a patent, whichever is required by the applicable patent laws.

Uses of the culture of mushroom line J10102-s69 include, among many other things, the production of hybrid mushroom cultures incorporating line J10102-s69, the production of mushrooms from cultures incorporating line J10102-s69, and the production of mushroom parts from cultures incorporating line J10102-s69. Still other uses include processes for making a mushroom culture that comprise mating homokaryotic *Agaricus bisporus* line J10102-s69 with another mushroom culture and processes for making a mushroom culture containing in its genetic material one or more traits introgressed into line J10102-s69 through introgressive trait conversion or transformation, and to the mushroom cultures, mushrooms, and mushroom parts produced by such introgression. Further, the invention may include a hybrid mushroom culture, mushroom, mushroom part, including a spore, or culture part produced by mating the homokaryotic line J10102-s69, or an introgressed trait conversion of line J10102-s69, with another mushroom culture. Still other uses of the present invention include the production of homokaryotic mushroom lines derived from mushroom line J10102-s69, as well as the processes for making other homokaryotic mushroom lines derived from mushroom line J10102-s69, and to the production of the inbred mushroom lines and their parts derived by the use of those processes.

With respect to spores, living spores are heterokaryons or homokaryons in a dormant state. Spores are one part of the mushroom organism. Other parts include caps, stems, gills, cells (defined as hyphal compartments incorporating nuclei, mitochondria, cytoplasm, a cell membrane, and a cell wall including crosswalls), hyphae, and mycelium. Spores may be aseptically collected on sterile material, suspended in sterile water at various dilutions, and plated onto sterile agar growth media in order to produce germinated spores and the cultures incorporated within the spores. A preferred technique is to have within the enclosed petri plate a living *Agaricus* culture which may stimulate spore germination via the diffusion of a volatile pheromone. Germinated spores may be isolated under a microscope using sterile microtools such as steel needles, onto fresh nutrient agar plates. Using this method, heterokaryotic and homokaryotic offspring of a heterokaryotic strain comprising the spores and the cultures incorporated within the spores of the heterokaryotic strain may be obtained.

Development of novel hybrid varieties via heteromixis comprises the controlled association and mating of two compatible cultures to obtain a novel heterokaryon culture. Homokaryons (='lines') are the preferred starting cultures for making matings as they have maximal ability to anastomose and achieve plasmogamy with other cultures. Heterokaryons may also be confronted but with commercially unreasonably low probabilities of a mating resulting in successful formation of a novel heterokaryon. Compatibility is determined by the genotype at the MAT locus; two homokaryons with the same MAT allele cannot establish a heterokaryon after anastomosis. In a defined mating program, homokaryotic lines are obtained and are associated in predetermined pairwise combinations. In one method, homokaryon pairs may be placed in close proximity on the surface of a nutrient agar medium in a petri dish and allowed to grow together (in a physical association), at which point anastomoses between the two cultures occur. A successful outcome is a mating. The novel hybrid heterokaryon may be obtained by transferring mycelium from the fusion zone of the dish. Such a paired mating method was used to develop hybrid heterokaryotic strains from line J10102-s69.

In contrast, EDVs are most often derived directly from a single initial culture (e.g., strain); all such derivations produce EDVs. There is no universally accepted definition of an EDV; one example of a definition applicable to plant varieties is provided by the US Plant Variety Protection Act (revised edition, February 2006). The definition employed herein is congruent with the term as it is widely understood. 'Essential derivation' methods of obtaining cultures which are by definition consequently EDVs of a single initial culture of *A. bisporus* include somatic selection, tissue culture selection, single spore germination, multiple spore germination, selfing, repeated mating back to the initial culture, mutagenesis, and transformation, to provide some examples. DNA-mediated transformation of *A. bisporus* has been reported by Velcko, A. J. Jr., Kerrigan, R. W., Mac-Donald, L. A., Wach, M. P., Schlagnhaufer, C., and Romaine, C. P. 2004, Expression of novel genes in *Agaricus bisporus* using an *Agrobacterium*-mediated transformation technique. Mush. Sci. 16: 591-597, and references therein, herein incorporated by reference. Transformation may introduce a single new gene or allele into the genome of an initial culture.

EDVs are unambiguously recognizable by their genotype, which will be predominantly a subset that of the single initial culture. Percentages of the initial genotype that will be present in *Agaricus bisporus* EDVs range from almost 100% in the case of somatic selections, to 99.x % in the case of strains modified by DNA-mediated transformation, to 90-99.x % in the case of single or multiple spore selections or some mutagenesis, to an average of from about 75 to about 85% in the case of sibling-offspring matings (=selfing). Many methods of genotype determination, including methods described below, and others well known in the art, may be employed to determine the percentage of DNA of an initial culture that is present in another culture.

Genotypic fingerprints are descriptions of the genotype at defined loci, where the presence of characterized alleles is recorded. Such fingerprints provide powerful and effective techniques for recognizing clones and all types of EDVs of an initial strain, as well as for recognizing ancestry within outbred lineages. Many techniques are available for defining and characterizing loci and alleles in the genotype. The most detailed approach is provided by whole-genome sequencing (WGS), which allows for direct characterization and comparison of DNA sequences across the entire genome. Using this approach to generate robust genotypic fingerprints incorporating large numbers of marker loci, it is possible to establish the nature of the relationship between two strains, including strains related by genealogical descent over several generations. Sylvan America, Inc. has tracked genetic markers through four to six generations of its breeding pedigrees. If a sufficient number of rare markers are present in an initial strain or line, it will be possible to identify descent from an initial strain or line after several outbred generations without undue experimentation. In a hypothetical example, the mean expectation for genomic representation of an initial haploid line after 4 outbred generations is 3.1% in an F4 hybrid, which corresponds to ca. 1 Mb of the nuclear genomic DNA of *A. bisporus*. Based on Sylvan America's analyses, that amount of DNA from each of two unrelated strains of *A. bisporus* may typically contain from about 10,000 to about 20,000 single nucleotide polymorphisms (SNPs), any one of which may provide a distinguishing marker linking the F4 hybrid to the initial line. By using multiple independent markers, ancestors of a strain can be identified with a very high probability of success and with high confidence.

The advantages of the present invention over existing prior art relating to *Agaricus bisporus* mushrooms and cultures, which shall become apparent from the description which follows, are accomplished by the invention as hereinafter described and claimed.

One or more aspects of the present invention may be provided by an *Agaricus bisporus* mushroom culture including at least one set of chromosomes of an *Agaricus bisporus* line J10102-s69, the culture of the line J10102-s69 having been deposited under the NRRL Accession Number 50893, wherein said chromosomes comprise all of the alleles of the line J10102-s69 at the sequence-characterized marker loci listed in Table I below. In one embodiment, the culture above may be an F1 hybrid *Agaricus bisporus* mushroom culture produced by mating the culture of the line J10102-s69 with a different *Agaricus bisporus* culture. Thus, it will be appreciated that, in one embodiment, a part of the culture of the line J10102-s69 above may be selected from the group consisting of hyphae, spores, and cells and parts of cells, including, nuclei, mitochondria, cytoplasm, protoplasts, DNA, RNA, proteins, cell membranes and cell walls, each part being present in either the vegetative mycelium of the culture or in mushrooms produced by the culture, or both. Further, in other embodiments, the culture of the line J10102-s69 above may be incorporated into products selected from mycelium, spawn, inoculum, casing inoculum, fresh mushrooms, processed mushrooms, mushroom extracts and fractions, mushroom pieces, and colonized substrates including grain, compost, and friable particulate matter. In other embodiments, the F1 hybrid mushroom culture of *Agaricus bisporus* above may be processed into one or more products selected from the group consisting of mycelium, spawn, inoculum, casing inoculum, fresh mushrooms, processed mushrooms, mushroom extracts and fractions, mushroom pieces, and colonized substrates including grain, compost, and friable particulate matter. In other embodiments, a mushroom may be produced by growing a crop of mushrooms from the culture of the line J10102-s69 above. In other embodiments, a mushroom may be produced by growing a crop of mushrooms from the F1 hybrid mushroom culture above. In further embodiments, an Essentially Derived Variety of the culture of line J10102-s69 is produced. In still other embodiments, an Essentially Derived Variety of the F1 hybrid mushroom culture above is produced.

One or more other aspects of the present invention may be provided by a process for introducing a desired trait into a culture of *Agaricus bisporus* line J10102-s69. Such a process may be initiated by (1) mating the culture of line J10102-s69 to a second culture of *Agaricus bisporus* having the desired trait, to produce a hybrid. The process further proceeds by (2) obtaining an offspring that carries at least one gene that determine the desired trait from the hybrid produced above. The process further includes (3) mating the offspring of the hybrid with the culture of line J10102-s69 to produce a new hybrid and (4) repeating the steps of (2) obtaining and (3) mating at least once to produce a subsequent hybrid. That is, step (4) may be repeated up to any of 1, 2, 3, 4, 5, 6, 7, 8, 9 and 10 times. In other embodiments, repeating steps (2) and (3) may occur more than 10 times. Upon completion of step (4), the process then provides (5) obtaining a homokaryotic line carrying at least one gene that determines the desired trait and comprises at least 75% of the alleles of line J10102-s69 at the sequence-characterized marker loci described in Table I, from the subsequent hybrid of step (4). In one embodiment, the homokaryotic line obtained may comprise 80% of the alleles of line J10102-s69 at the sequence-characterized marker loci described in Table I. In other embodiments, the homokaryotic line obtained may comprise 85%, 90%, 95%, 96%, 97%, 98%, 99% or may be comprise essentially 100% of the alleles of line J10102-s69 at the sequence-characterized marker loci described in Table I.

Still one or more other aspects of the present invention may be provided by a process of producing a hybrid mushroom culture. The process includes mating a first mushroom culture with a second mushroom culture, wherein at least one of the first and second mushroom cultures is an *Agaricus bisporus* culture having all of the physiological and morphological characteristics of line J10102-s69, wherein the culture of said line J10102-s69 was deposited under the NRRL Accession Number 50893. In one embodiment, a hybrid culture is produced by this process. In another embodiment, a hybrid mushroom, or its parts, may be produced by growing a crop of mushrooms from the hybrid culture above. In yet another embodiment, a part of the hybrid culture above may be selected from the group consisting of hyphae, mushrooms, spores, cells, nuclei, mitochondria, cytoplasm, protoplasts, DNA, RNA, proteins, cell membranes and cell walls. In other embodiments, the hybrid culture of *Agaricus bisporus* above may be incorporated into one or more products selected from the group consisting of mycelium, spawn, inoculum, casing inoculum, fresh mushrooms, processed mushrooms, mushroom extracts and fractions, mushroom pieces, and colonized substrates including grain, compost, and friable particulate matter.

Still one or more other aspects of the present invention may be provided by an *Agaricus bisporus* culture having all of the physiological and morphological characteristics of line J10102-s69, wherein the culture of said line J10102-s69 was deposited under the NRRL Accession Number 50893. In one embodiment, the culture may further include a marker profile in accordance with the marker profile of line J10102-s69 shown in Table I. In one or more embodiments, the culture above provides a cell. In one or more embodiments, the cell above may further include a marker profile in accordance with the profile of line J10102-s69 shown in Table I. In other embodiments, a spore may comprise the cell above. In other embodiments, the hybrid culture above may be further defined as having a genome including a single locus trait conversion. In further embodiments, the locus above may be selected from the group consisting of a dominant allele and a recessive allele. In one or more other embodiments, the locus above may confer a trait selected from the group consisting of mushroom size, mushroom shape, mushroom cap roundness, mushroom flesh thickness, mushroom color, mushroom surface texture, mushroom cap smoothness, tissue density, tissue firmness, delayed maturation, basidial spore number greater than two, sporelessness, increased dry matter content, increased shelf life, reduced brusing, increased yield, altered distribution of yield over time, decreased spawn to pick interval, resistance to infection by symptoms of or transmission of bacterial, viral or fungal disease or diseases, insect resistance, nematode resistance, ease of crop management, suitability of crop for mechanical harvesting, canning and/or processing, desired behavioral response to environmental conditions, to stressors, to nutrient substrate composition, to seasonal influences, and to farming practices.

Still one or more other aspects of the present invention may be provided by a method of producing a mushroom culture. The method includes (a) growing a progeny culture produced by mating the culture having all of the physiological and morphological characteristics of line J10102-s69, wherein the culture of said line J10102-s69 was deposited under the NRRL Accession Number 50893, with a second *Agaricus bisporus* culture; (b) mating the progeny culture with itself or a different culture to produce a progeny culture of a subsequent generation; (c) growing a progeny culture of a subsequent generation and mating the progeny culture of a subsequent generation with itself or a different culture; and (d) repeating steps (b) and (c) for an additional 0, 1, 2, 3, 4 or 5 (i.e., 0-5) generations to produce a mushroom culture. In one embodiment, the produced mushroom culture above is an inbred culture. In one or more other embodiments, the method above may further include the step of mating the inbred culture with a second, distinct culture to produce an F1 hybrid culture.

Yet one or more other aspects of the present invention may be provided by a method for developing a second culture in a mushroom strain development program. Such a method includes applying mushroom strain development techniques to a first mushroom culture, or parts thereof, wherein the first mushroom culture is a culture having all of the physiological and morphological characteristics of line J10102-s69, wherein the culture of said line J10102-s69 was deposited under the NRRL Accession Number 50893. It is the application of the mushroom strain development techniques that results in the development of the second culture. Such known mushroom strain development techniques are selected from the group consisting of inbreeding, outbreeding, selfing, introgressive trait conversions, essential derivation, pedigree-assisted breeding, marker assisted selection, and transformation.

Finally, another aspect of the present invention may be provided by a method of mushroom strain development. This method includes obtaining a molecular marker profile of *Agaricus bisporus* mushroom line J10102-s69, a culture of which was deposited under the NRRL Accession Number 50893. Another step of the method includes obtaining an F1 hybrid culture, for which the deposited mushroom culture of the *Agaricus bisporus* mushroom line J10102-s69 is a parent. Once the F1 hybrid culture is obtained, a further step of mating a culture obtained from the F1 hybrid culture with a different mushroom culture is employed. Once this is done, the selection of progeny that possess characteristics of the molecular marker profile of line J10102-s69 as above may be conducted to complete the method using known techniques.

DETAILED DESCRIPTION OF THE INVENTION

Initially, in order to provide clear and consistent understanding of the specification and claims, including the scope to be given such terms, the following definitions are provided.

Allele: A heritable unit of the genome at a defined locus, ultimately identified by its DNA sequence (or by other means).

Amphithallism: A reproductive syndrome in which heteromixis and intramixis are both active.

Anastomosis: Fusion of two or more hyphae that achieves cytoplasmic continuity.

Basidiomycete: A monophyletic group of fungi producing meiospores on basidia; a member of a corresponding subdivision of Fungi such as the Basidiomycetales or Basidiomycotina.

Basidium: The meiosporangial cell, in which karyogamy and meiosis occur, and upon which the basidiospores are formed.

Bioefficiency: For mushroom crops, the net fresh weight of the harvested crop divided by the dry weight of the compost substrate at the time of spawning, for any given sampled crop area or compost weight.

Breeding: Development of strains, lines or varieties using methods that emphasize sexual mating.

Cap: Pileus; part of the mushroom, the gill-bearing structure.

Cap Roundness: Strictly, a ratio of the maximum distance between the uppermost and lowermost parts of the cap, divided by the maximum distance across the cap, measured on a longitudinally bisected mushroom; typically averaged over many specimens; subjectively, a 'rounded' property of the shape of the cap.

Carrier substrate: A medium having both nutritional and physical properties suitable for achieving both growth and dispersal of a culture.

Casing layer, casing: A layer of non-nutritive material such as peat or soil that is applied to the upper surface of a mass of colonized compost in order to permit development of the mushroom crop.

Casing inoculum (CI): A formulation of inoculum material incorporating a mushroom culture, typically of a defined heterokaryotic strain, suitable for mixing into the casing layer.

Cloning: Somatic propagation without selection.

Combining ability: The capacity of an individual to transmit traits or superior performance to its offspring (known and available methods of assessment vary by trait).

Compatibility: See heterokaryon compatibility.

Culture: The tangible living organism; the organism propagated on various growth media and substrates; one instance of one physical strain, line, homokaryon or heterokaryon; the sum of all of the parts of the culture, including hyphae, mushrooms, spores, cells, protoplasts, nuclei, mitochondria, cytoplasm, DNA, RNA, and proteins, cell membranes and cell walls.

Derivation: Development from a strain; see Essentially Derived Variety (EDV).

Derived lineage group: The set of EDVs derived from a single initial strain or variety.

Descent: Genealogical descent over a limited number (e.g., 10 or fewer) of generations.

Diploid: Having two haploid chromosomal complements within a single nuclear envelope.

Essential derivation: A process by which an Essentially Derived Variety is obtained from an initial variety or strain or from an EDV of an initial variety or strain; modification of an initial culture using methods including somatic selection, tissue culture selection, selfing including intramictic reproduction via single spores and multiple spores and mating of sibling offspring lines, back-mating to the initial variety, or mutagenesis and/or genetic transformation of the initial variety to produce a distinct culture in which the genotype of the resulting culture is predominantly that of the initial culture.

Essentially Derived Variety (EDV): (Note: EDV definitions incorporate elements of (1) relatedness, (2) methods of derivation, (3) and empirical tests.) In general, a variety that is predominantly derived from an initial variety or from an EDV of an initial variety, and which conforms to essential characteristics of the initial variety except for distinguishing differences resulting from the act of derivation, is an EDV of the initial variety. In the art of mushroom strain development, a strain or culture predominantly or entirely derived from a single initial strain or culture, thus having most or all, but at least 75%, of its genome or genotype present in the genome or genotype of the initial strain or culture; a strain or culture obtained from an initial strain or culture by somatic selection, tissue culture selection, selfing including mating of sibling offspring lines and intramictic reproduction via single or multiple spores, back-mating to the initial strain or culture, or mutagenesis and/or genetic transformation of the initial strain or culture; a strain or culture reconstituted from neohaplonts derived from an initial strain or culture, whether or not the haploid lines have been passed into or out of other heterokaryons; a strain or culture with the same essential phenotype as that of an initial strain or culture.

Flesh Thickness: A ratio of the maximum distance between the top of the stem and the uppermost part of the cap, divided by the maximum distance across the cap, measured on a longitudinally bisected mushroom; typically averaged over many specimens; subjectively called 'meatiness'.

Flush: A period of mushroom production within a cropping cycle, separated by intervals of non-production; the term flush encompasses the terms 'break' and 'wave' and can be read as either of those terms.

Fungus: An organism classified as a member of the Kingdom Fungi.

Genotypic fingerprint: A description of the genotype at a defined set of marker loci; the known genotype.

Gill: Lamella; part of the mushroom, the hymenophore- and basidium-bearing structure.

Haploid: Having only a single complement of nuclear chromosomes; see homokaryon.

Heteroallelic: Having two different alleles at a locus; analogous to heterozygous.

Heteroallelism: Differences between homologous chromosomes in a heterokaryotic genotype; analogous to heterozygosity.

Heterokaryon: As a term of art this refers to a sexual heterokaryon: a culture which has two complementary (i.e., necessarily heteroallelic at the MAT locus) types of haploid nuclei in a common cytoplasm, and is thus functionally and physiologically analogous to a diploid individual (but cytogenetically represented as N+N rather than 2N), and which is potentially reproductively competent, and which exhibits self/non-self incompatibility reactions with other heterokaryons; also called a strain or stock in the breeding context.

Heterokaryon compatibility: The absence of antagonism observed during physical proximity or contact between two heterokaryons that are not genetically identical; see Heterokaryon Incompatibility.

Heterokaryon incompatibility: The phenomenon of antagonism observed during physical proximity or contact between two heterokaryons that are not genetically identical; a multilocus self/non-self recognition system that operates in basidiomycete heterokaryons.

Heterokaryotic: Having the character of a heterokaryon.

Heteromixis: Life cycle involving mating between two different non-sibling haploid individuals or gametes; outbreeding.

Homoallelic: Having not more than one allele at a locus. The equivalent term in a diploid organism is 'homozygous'. Haploid lines are by definition entirely homoallelic at all non-duplicated loci.

Homokaryon: A haploid culture with a single type (or somatic lineage) of haploid nucleus (cytogenetically represented as N), and which is ordinarily reproductively incompetent, and which does not exhibit typical self/non-self incompatibility reactions with heterokaryons, and which may function as a gamete in sexually complementary anastomoses; a 'line' which, as with an inbred plant line, transmits a uniform genotype to offspring; a predominantly homoallelic line that mates well and fruits poorly is a putative homokaryon for strain development purposes; see discussion below.

Homokaryotic: Having the character of a homokaryon; haploid.

Hybrid: Of biparental origin, usually applied to heterokaryotic strains and cultures produced in controlled matings.

Hybridizing: Physical association, for example on a petri dish containing a sterile agar-based nutrient medium, of two cultures, usually homokaryons, in an attempt to achieve anastomosis, plasmogamy, and formation of a sexual heterokaryon (=mating); succeeding in the foregoing.

Hyphae: Threadlike elements of mycelium, composed of cell-like compartments.

Inbreeding: Matings that include sibling-line matings, back-matings to parent lines or strains, and intramixis; reproduction involving parents that are genetically related.

Incompatibility: See heterokaryon incompatibility.

Inoculum: A culture in a form that permits transmission and propagation of the culture, for example onto new media; specialized commercial types of inoculum include spawn and CI.

Intramixis: A uniparental sexual life cycle involving formation of a complementary 'mated' pair of postmeiotic nuclei within the basidium or individual spore.

Introgressive trait conversion: mating offspring of a hybrid to a parent line or strain such that a desired trait from one strain is introduced into a predominating genetic background of the other parent line or strain.

Lamella: see 'gill'.

Line: A culture used in matings to produce a hybrid strain; ordinarily a homokaryon which is thus homoallelic, otherwise a non-heterokaryotic (non-NSNPP) culture which is highly homoallelic; practically, a functionally homokaryotic and entirely or predominantly homoallelic culture; analogous in plant breeding to an inbred line which is predominantly or entirely homozygous.

Lineage group: see 'derived lineage group'. The set of EDVs derived from a single initial strain or variety.

Locus: A defined contiguous part of the genome, homologous although often varying among different genotypes; plural: loci.

Marker assisted selection: Using linked genetic markers including molecular markers to track trait-determining loci of interest among offspring and through pedigrees.

MAT: The mating-type locus, which determines sexual compatibility and the heterokaryotic state.

Mating: The sexual union of two cultures via anastomosis and plasmogamy; methods of obtaining matings between mushroom cultures are well known in the art.

Mycelium: The vegetative body or thallus of the mushroom organism, comprised of threadlike hyphae.

Mushroom: The reproductive structure of an agaric fungus; an agaric; a cultivated food product of the same name.

Neohaplont: A haploid culture or line obtained by physically deheterokaryotizing (reducing to haploid components) a heterokaryon; a somatically obtained homokaryon.

Offspring: Descendents, for example of a parent heterokaryon, within a single generation; most often used to describe cultures obtained from spores from a mushroom of a strain.

Outbreeding: Mating among unrelated or distantly related individuals.

Parent: An immediate progenitor of an individual; a parent strain is a heterokaryon; a parent line is a homokaryon; a heterokaryon may be the parent of an F1 heterokaryon via an intermediate parent line.

Pedigree-assisted breeding: The use of genealogical information to identify desirable combinations of lines in controlled mating programs.

Phenotype: Observable characteristics of a strain or line as expressed and manifested in an environment.

Plasmogamy: Establishment, via anastomosis, of cytoplasmic continuity leading to the formation of a sexual heterokaryon.

Progenitor: Ancestor, including parent (the direct progenitor).

Selfing: Mating among sibling lines; also intramixis.

Somatic: Of the vegetative mycelium.

Spawn: A mushroom culture, typically a pure culture of a heterokaryon, typically on a sterile substrate which is friable and dispersible particulate matter, in some instances cereal grain; commercial inoculum for compost; reference to spawn includes reference to the culture on a substrate.

Spore: Part of the mushroom, the reproductive propagule.

Stem: Stipe; part of the mushroom, the cap-supporting structure.

Sterile Growth Media: Nutrient media, sterilized by autoclaving or other methods, that support the growth of the organism; examples include agar-based solid nutrient media such as Potato Dextrose Agar (PDA), nutrient broth, and many other materials.

Stipe: see 'stem'.

Strain: A heterokaryon with defined characteristics or a specific identity or ancestry; equivalent to a variety.

Tissue culture: A de-differentiated vegetative mycelium obtained from a differentiated tissue of the mushroom.

Trait conversion: Selective introduction of the genetic determinants of one (a single-locus conversion) or more desirable traits into the genetic background of an initial strain while retaining most of the genetic background of the initial strain. See 'Introgressive trait conversion' and 'Transformation'.

Transformation: A process by which the genetic material carried by an individual cell is altered by the incorporation of foreign (exogenous) DNA into its genome; a method of obtaining a trait conversion including a single-locus conversion.

Virus-breaking: Using multiple incompatible strains, i.e. strains exhibiting heterokaryon incompatibility, successively in a program of planned strain rotation within a mushroom production facility to reduce the transmission of virus from on-site virus reservoirs into newly planted crops.

Yield: The net fresh weight of the harvest crop, normally expressed in pounds per square foot.

Yield pattern: The distribution of yield within each flush and among all flushes; influences size, quality, picking costs, and relative disease pressure on the crop and product.

With respect to the definition of homokaryon above, it is noted that homokaryons and homoallelic lines are subject to technical and practical considerations: A homokaryon in classical terms is a haploid culture which is axiomatically entirely homoallelic. In practical terms, for fungal strain development purposes, the definition is broadened somewhat to accommodate both technical limitations and cytological variation, by treating all predominately homoallelic lines as homokaryons. Technical limitations include the fact that genomes contain duplicated DNA regions including repeated elements such as transposons, and may also include large duplications of chromosomal segments due to historical translocation events. Two different *A. bisporus* genomes sequenced by the Joint Genome Institute, a U.S. federal facility, differ in estimated length by 4.4%, and in gene numbers by 8.2%, suggesting a considerable amount of DNA duplication or rearrangement within different strains of the species. No presently available genome of *A. bisporus* can completely account for the physical arrangement of such elements and translocations, and so the assembled genome sequences of haploid lines may have regions that appear to be heteroallelic using currently available genotyping methods. Cytologically, a homokaryotic offspring will ordinarily be a spore that receives one haploid, postmeiotic nucleus. However, a spore receiving two third-division nuclei from the basidium will be genetically equivalent to a homokaryon. A spore receiving two second-division 'sister' postmeiotic nuclei will be a functional homokaryon even though some distal 'islands' of heteroallelism may be present due to crossovers during meiosis. Also, a meiosis that has an asymmetrical separation of homologues can produce an aneuploid, functionally homokaryotic spore in which an extra chromosome, producing a region of heteroallelism, is present. All of these cultures are highly homoallelic and all function as homokaryons. Technological limitations make it impractical to distinguish among such cultures, and also to rule out DNA segment duplication as an explanation for limited, isolated regions of the genome sequence assembly that appear to be heteroallelic. Therefore, in the present application, the use of the term 'homoallelic' to characterize a line includes entirely or predominately homoallelic lines, and cultures described in this way are functional homokaryons, are putatively homokaryotic, and are all defined as homokaryons in the present application.

Now, with respect to the invention and as noted hereinabove, the present invention relates to a homokaryotic line, and more specifically, a line of *Agaricus bisporus* designated J10102-s69, and methods for using the line designated J10102-s69. A culture of the line designated J10102-s69 has been deposited with the Agricultural Research Services Culture Collection (NRRL) 1815 North University Street, Peoria, Ill. 61604 USA ("NRRL") as Accession No. 50893.

*Agaricus bisporus* mushroom line J10102-s69 is a haploid filamentous basidiomycete culture which in vegetative growth produces a branching network of hyphae, i.e. a mycelium. Growth can produce an essentially two-dimensional colony on the surface of solidified (e.g., agar-based) media, or a three-dimensional mass in liquid or solid-matrix material. The morphological and physiological characteristics of line J10102-s69 in culture on Difco brand PDA medium are provided as follows. Line J10102-s69 growing on PDA medium in a 10 cm diameter Petri dish produced a light brown-yellow or 'tan' colored irregularly lobate colony with a roughly circular overall outline that increased in diameter by (0.3-0.4-) 0.7 (-0.8-1.4) mm/day during dynamic equilibrium-state growth between days 12 and 26 after inoculation using a 6.5-7 mm diameter circular plug of the culture on PDA as inoculum. Hyphae of the culture on Difco PDA were irregular and about cylindrical, measured (12-) 41-71 (-99)×(4.5-) 6-8 (-10) um, and exhibited a wide range of branching angles from about 10 to 90 degrees off the main hyphal axis.

Line J10102-s69 can be used to produce hybrid cultures with desirable productivity, timing, appearance, and other agronomic traits as is required of successful commercial mushroom strains, while also providing more diversified, non-cultivar germplasm. Line J10102-s69 has been found to have an advantageous genotype for mating to produce commercially useful hybrid strains. Several useful stocks have contributed to the genome of line J10102-s69. Line J10102-s69 has, for example, a mating-type allele 2 on scaffold 1 contributed by the traditional smooth-white stock, and a 'white' color determining allele, as reported by allele E1 at the MFPC-1-ELF marker locus on scaffold 8, contributed by the traditional off-white hybrid stock. Among the remaining genomic scaffolds are at least three (i.e., scaffolds 2, 9 and 10) contributed by other, wild stocks in the pedigree. In combination, these diverse genetic contributions were observed to have combined to produce a superior line with excellent combining ability in matings.

The J10102-s69 line is haploid and thus is entirely homoallelic (although some limited regions of duplicated DNA may be present in its genome). The line has shown uniformity and stability in culture. The line has been increased by transfer of pure inocula into larger volumes of sterile culture media. No variant traits have been observed or are expected in line J10102-s69.

Mushroom cultures are most reliably identified by their genotypes, in part because successful cultivar strains are required by the market to conform to a narrow phenotypic range. The genotype can be characterized through a genetic marker profile, which can identify isolates (subcultures) of the same line, strain or variety, or a related variety including a variety derived entirely from an initial variety (i.e., an Essentially Derived Variety), or can be used to determine or validate a pedigree.

Means of obtaining genetic marker profiles using diverse techniques including whole genome sequencing are well known in the art. The whole genomic sequence of line J10102-s69 has been obtained by Sylvan America, Inc., and consequently, about 93%-95% (about 28 Mb) of the entire genotype of line J10102-s69 is known to the Assignee with certainty. The total number of markers distinguishing line J10102-s69 that are known to the assignee is about 300,000. A brief excerpt of the genotype of line J10102-s69 at numerous sequence-characterized marker loci distributed at intervals along each of the 13 chromosomes is provided in Table I.

TABLE I

| Scaffold | Position of SNP [H97 V2.0 ref. coords.] | Culture: J10102-s69 | OWNC | J11500 |
|---|---|---|---|---|
| 1 | 99995 | CTAGTTGA | CTACATTGA | CTACTTGA |
| 1 | 349966 | AAGCGGTT | AAGGTGGTT | AAGGYGGTT |
| 1 | 600059 | TTTTCTTTA | TTTTTTTT-C | TTTTYTT[-/A] |
| 1 | 850014 | CTTTTCGC | CCTTTTCAC | CYTTTTCYC |

TABLE I-continued

| Scaffold | Position of SNP [H97 V2.0 ref. coords.] | Culture: J10102-s69 | OWNC | J11500 |
|---|---|---|---|---|
| 1 | 1099971 | GTCG CACC | GTCGACACC | GTCG RCACC |
| 1 | 1350278 | GGAG TTCG | GGAGAGTCG | GGAG RKTCG |
| 1 | 1599956 | AATA GCGC | AATAAGCGC | AATA RGCGC |
| 1 | 1850032 | CGA CAATT | CGAGTAATT | CGAG YAATT |
| 1 | 2119049 | ACA CTCAA | ACAATCCAA | ACAA YYCAA |
| 1 | 2400243 | ACTT GATGA | ACTTCATGA | ACTT SATGA |
| 1 | 2612870 | AATA AGAGT | AATAGGAGT | AATA RGAGT |
| 1 | 2858975 | GCCC CTCTT | GCCGTTCTT | GCCG YTCTT |
| 1 | 2804522 | GAAG GGAC | GAAGACGAC | GAAG RSGAC |
| 1 | 3047987 | AAGG AGGGG | AAGGGGGGG | AAGG RGGGG |
| 1 | 3164166 | ATA TCGGG | ATAAGGGG | ATAA KSGGG |
| 1 | 3256057 | TATC CGTTT | TATCTGTTT | TATC YGTTT |
| 2 | 101820 | ATTA CGGAT | ATTAAAGAT | ATTA MRGAT |
| 2 | 350156 | TCGG AGGTG | TCGGGGGTG | TCGG RGGTG |
| 2 | 600112 | ATGT GTACG | ATGTATACG | ATGT RTACG |
| 2 | 850338 | TGGT TCTAA | TGGTGCTAA | TGGT KCTAA |
| 2 | 1099413 | CCTG GCTCA | CCTGACTCA | CCTG RCTCA |
| 2 | 1349512 | CTCA ACAGT | CTCAGCAGT | CTCA RCAGT |
| 2 | 1600085 | CACA TTGCC | CACAATGCC | CACA WTGCC |
| 2 | 1901773 | ACTC AAATT | ACTCGAATT | ACTC RAATT |
| 2 | 2150201 | GTCG AAGGT | GTCGTAGGT | GTCG WAGGT |
| 2 | 2400281 | TCA CACTC | TCAAAACCC | TCAA MACYC |
| 2 | 2650136 | ATAA ATCCT | ATAATTCCT | ATAA WTCCT |
| 2 | 2903593 | ACTA TAGGA | ACTAAAGA | ACTA WARGA |
| 2 | 3048019 | GTCC ACTGC | GTCCGCTGC | GTCC RCTGC |
| 3 | 65650 | GGCG GTTTT | GGCGCTTTT | GGCG STYTT |
| 3 | 119281 | TTTA CACTC | TTTATACTC | TTTA YACTC |
| 3 | 249570 | GTAT TATGT | GTAT TATGT | GTAT TATGT |
| 3 | 750000 | GTCC GGCCA | GTCC GGCCA | GTCC GGCCA |
| 3 | 1250000 | TTTT TCCGG | TTTT TCCGG | TTTT TCCGG |
| 3 | 1750000 | ACGC CTGAC | ACGC CTGAC | ACGC CTGAC |
| 3 | 2250000 | CGTG GCGAT | CGTG GCGAT | CGTG GCGAT |
| 3 | 2520748 | TAAT TCCAC | TAATGCCAC | TAAT KCCAC |
| 4 | 100004 | GAGT AATGA | GAGTGATAA | GAGT RATRA |
| 4 | 340893 | AGGA GGTAC | AGGTGGTAT | AGG RGGTAY |
| 4 | 598147 | GATC AACAG | GATCGACAG | GATC RACAG |
| 4 | 852119 | CGA CACTC | CGAATATTC | CGAA YAYTC |

TABLE I-continued

| Scaffold | Position of SNP [H97 V2.0 ref. coords.] | Culture: J10102-s69 | OWNC | J11500 |
|---|---|---|---|---|
| 4 | 1100085 | GATG*A*CGAA | GATGCCGAA | GATG*m*CGAA |
| 4 | 1350536 | CGAA*AC*CGG | CGAACTCGG | CGAA*my*CGG |
| 4 | 1599885 | GATA*A*TTGC | GATACTTGC | GATA*m*TTGC |
| 4 | 1850288 | ATTC*AC*GTA | ATTCGTGTA | ATTC*ry*GTA |
| 4 | 2100356 | TCAG*G*ACC | TCAGAGACC | TCAG*r*GACC |
| 4 | 2284257 | TCTG*A*ACTG | TCTGGACTG | TCTG*r*ACTG |
| 5 | 100211 | TCCT*C*GAAT | TCCTTGAAT | TCCT*y*GAAT |
| 5 | 350872 | GGCC*C*GCCC | GGCGTGCCC | GGCG*y*GCCC |
| 5 | 599922 | CGTC*G*TTCA | CGTCATTCA | CGTC*r*TTCA |
| 5 | 851262 | TAAT*CG*TCT | TAATTCTCT | TAAT*ys*TCT |
| 5 | 1099776 | ACAT*C*GACA | ACATTGACA | ACAT*y*GACA |
| 5 | 1352539 | TTGT*TG*TCC | TTGTGATCC | TTGT*kr*TCC |
| 5 | 1599904 | AACT*C*CCTT | AACTTCCTT | AACT*y*CCTT |
| 5 | 1851458 | AAAT*TC*TCC | AAATAATCC | AAAT*wm*TCC |
| 5 | 2100025 | CCCT*C*AGTC | CCCTTAGTC | CCCT*y*AGTC |
| 5 | 2278878 | GGTC*A*AAAA | GGTCGAAAA | GGTC*r*AAAA |
| 6 | 106294 | GCCA*CC*TC*A* | GCCATCTCG | GCCA*y*CTC*r* |
| 6 | 350337 | CATT*C*GGTT | CATTTGGTT | CATT*y*GGTT |
| 6 | 600047 | GGAG*T*ATTT | GGAGCATTT | GGAG*y*ATTT |
| 6 | 849990 | AGTT*T*AGGA | AGTTCAGGA | AGTT*y*AGGA |
| 6 | 1098535 | CAAA*A*ATTG | CAAAGATTG | CAAA*r*ATTG |
| 6 | 1349453 | TGTC*AA*TAG | TGTCGGTAG | TGTC*rr*TAG |
| 6 | 1600000 | AAAC*C*TGGA | AAAC*C*TGGA | AAAC*C*TGGA |
| 6 | 1764645 | AACC*A*GATT | AACCGGATT | AACC*r*GATT |
| 6 | 2000087 | GATT*T*TGCG | GATTTTGCG | GATT*y*TGCG |
| 6 | 2252662 | GGGT*C*GGTA | GGGTTGGTA | GGGT*y*GGTA |
| 7 | 100284 | GAA*AC*TCAG | GAAATTCAG | GAAA*y*TCAG |
| 7 | 350044 | ATAT*C*CTTT | ATATTCTTT | ATAT*y*CTTT |
| 7 | 600111 | CAAT*C*ATTA | CAATTATTA | CAAT*y*ATTA |
| 7 | 850516 | TGAC*A*CATA | TGACGCATA | TGAC*r*CATA |
| 7 | 1100248 | TCAC*A*GAAG | TCACGGAAG | TCAC*r*GAAG |
| 7 | 1350089 | CTTT*C*CCCC | CTTTTCCCC | CTTT*y*CCCC |
| 7 | 1605047 | ATAC*GTG*AC | ATACTTGGC | ATAC*ktr*C |
| 7 | 1850000 | GAGA*T*ACT | GAGA*T*ACT | GAGA*T*ACT |
| 7 | 1898793 | TCCG*TATG*A | TCCGCATAA | TCCG*yatr*A |
| 7 | 1991505 | TCTA*AA*GTT | TCTACGGTT | TCTA*mr*GTT |

TABLE I-continued

| Scaffold | Position of SNP [H97 V2.0 ref. coords.] | Culture: J10102-s69 | OWNC | J11500 |
|---|---|---|---|---|
| 8 | 350000 | ATTG*A*CGCG | ATTG*A*CGCG | ATTG*A*CGCG |
| 8 | 600000 | CATT*G*ACGG | CATT*G*ACGG | CATT*G*ACGG |
| 8 | 1100000 | CATA*C*GATC | CATA*C*GATC | CATA*C*GATC |
| 8 | 1350000 | AGCT*T*AACA | AGCT*T*AACA | AGCT*T*AACA |
| 8 | 1600100 | CTGA*A*CCCT | CTGA*A*CCCT | CTGA*A*CCCT |
| 9 | 100105 | CTCA*G*CCGA | CTCAACCGA | CTCA*r*CCGA |
| 9 | 352455 | AGTC*TC*CCA | AGTCCTCCA | AGTC*yy*CCA |
| 9 | 599950 | TGGT*G*TCCC | TGGTATCCC | TGGT*r*TCCC |
| 9 | 1010845 | GGGT*A*GTGA | GGGTGGTGA | GGGT*r*GTGA |
| 9 | 1244202 | GATG*G*AGAT | GATGAAGAT | GATG*r*AGAT |
| 9 | 1504476 | TACT*A*TACC | TACTGTACC | TACT*r*TACC |
| 9 | 1656962 | TATC*C*ACTG | TATCTACTG | TATC*y*ACTG |
| 10 | 100438 | AATT*C*ATTT | AATTAATTT | AATT*m*ATTT |
| 10 | 350030 | GCGG*T*TCAA | GCGGCTCAA | GCGG*Y*TCAA |
| 10 | 600032 | TTAC*G*CTGG | TTACACTGG | TTAC*r*CTGG |
| 10 | 850000 | TCGG*T*CGGA | TCGG*T*CGGA | TCGG*T*CGGA |
| 10 | 860249 | CCGC*G*AAATT | CCGCAAATT | CCGC*r*AAATT |
| 10 | 1109960 | AGGA*G*ATGA | AGGAAATGA | AGGA*r*ATGA |
| 10 | 1303902 | TGAT*C*TACT | TGATTTACT | TGAT*y*TACT |
| 10 | 1490452 | AATC*T*GATG | AATCAGATG | AATC*w*GATG |
| 11 | 100000 | TATT*C*TTAG | TATT*C*TTAG | TATT*C*TTAG |
| 11 | 350000 | GTCA*G*CAAG | GTCA*G*CAAG | GTCA*G*CAAG |
| 11 | 600000 | ATGG*G*CGCG | ATGG*G*CGCG | ATGG*G*CGCG |
| 11 | 850000 | CTTC*C*CCAT | CTTC*C*CCAT | CTTC*C*CCAT |
| 11 | 1100000 | TTAC*A*GTTG | TTAC*A*GTTG | TTAC*A*GTTG |
| 11 | 124000 | AGCC*A*AGTA | AGCC*A*AGTA | AGCC*A*AGTA |
| 12 | 100000 | CCTT*C*TAGT | CCTT*C*TAGT | CCTT*C*TAGT |
| 12 | 1000000 | CGAG*G*AGGA | CGAG*G*AGGA | CGAG*G*AGGA |
| 13 | 100697 | ACGT*A*TTTA | ACGTCTTTA | ACGT*m*TTTA |
| 13 | 370521 | TTTG*T*GTCA | TTTGAGTCA | TTTG*w*GTCA |
| 13 | 604345 | CTTC*C*GCAT | CTTCAGCAT | CTTC*m*GCAT |
| 13 | 850249 | GG*T*TG*G*TG*A* | GGCTAGTAA | GG*y*TG*r*GT*r*A |
| 14 | 113109 | AGGG*G*AATA | AGGGAAATA | AGGG*r*AATA |
| 14 | 372086 | CGAT*C*T*T*TT | CGATCCCTT | CGAT*y*C*y*TT |
| 14 | 725684 | ATGA*A*TT*T*G | ATGAGTTCG | ATGA*r*TT*y*G |
| 15 | 150013 | GTGG*A*CCGT | GTGGCCCGT | GTGG*m*CCGT |
| 15 | 449866 | GAAT*C*TCGG | GAATTTCGG | GAAT*y*TCGG |

TABLE I-continued

| Scaffold | Position of SNP [H97 V2.0 ref. coords.] | Culture: J10102-s69 | OWNC | J11500 |
|---|---|---|---|---|
| 16 | 208609 | CACA*C*GCAC | CACATGCAC | CACA*Y*GCAC |
| 16 | 400000 | CCTC*G*GATT | CCTC*G*GATT | CCTC*G*GATT |
| 17 | 120000 | TATT*C*TTCA | TATT*C*TTCA | TATT*C*TTCA |
| 17 | 338415 | TGAG*G*AGCC | TGAGAAGCC | TGAG*r*AGCC |
| 17 | 449833 | ATCA*A*AC*T*A | ATCAGACAA | ATCA*r*AC*w*A |
| 18 | 101884 | ATTA*T*GGAC | ATTACGGAC | ATTA*y*GGAC |
| 19 | 98377 | GCTA*C*TGGG | GCTATTGGG | GCTA*C*TGGG |

Table I presents a 'fingerprint' excerpted from the SNP (Single Nucleotide Polymorphism) genotype of the entire genome sequences of line J10102-s69, of line OWNC, and of the F1 hybrid J11500 strain obtained from the mating of lines J10102-s69 and OWNC. It will be appreciated that the use of J10102-s69 in conjunction with line OWNC to provide strain J11500 is but one example of the F1 hybrid generation, it being noted that J10102-s69 has been used in at least 71 matings with other lines of *Agaricus bisporus* to produce F1 hybrids. The IUPAC nucleotide and ambiguity codes are used to represent the observed 9-base DNA marker sequences reported above, each of which represents a genotypic marker locus. The identity of each marker locus is specified by the scaffold and SNP position information derived from the H97 V2.0 reference genome sequence published by the U.S. Department of Energy Joint Genome Institute (Morin et al. 2012). Distinctions between the homoallelic genotypes of line J10102-s69 and line OWNC are evident, as is the composite relationship of the example heteroallelic genotype of strain J11500 to those of its two parental lines.

Genotype data for six additional marker loci is provided in TABLE II.

TABLE II

Alleles of J10102-s69 at 6 marker loci, for lines J10102-s69, OWNC, and SWNC

| Line | Marker: ITS | p1n150 | MFPC-1-ELF | AN | AS | FF |
|---|---|---|---|---|---|---|
| J10102-S69 | 4 | 2 | E1 | N5 | SC | FF1 |
| OWNC | 1 | 1T | E1 | N1 | SD | FF1 |
| SWNC | 2 | 2 | E2 | N2 | SC | FF2 |

OWNC and SWNC are two lines derived from two traditional white-capped cultivar stocks, as described in the concurrently filed patent application entitled "Hybrid Mushroom Strain J11500 and Descendants Thereof," the disclosure of which is incorporated by reference. Each is genotypically distinct, as shown in Table II.

Line J10102-s69 can be identified through its molecular marker profile as shown in Tables I and II. A culture or product incorporating the genetic marker profile shown in Tables I and II is an embodiment of the invention. Another embodiment of this invention is an *Agaricus bisporus* line or its parts comprising the same alleles as the line J10102-s69 for at least 75% of the loci listed in Tables I and II. In other embodiments, this line or its parts comprises the same alleles as the line J10102-s69 for at least 80%, 85%, 90%, 95%, 96%, 97%, 98%, 99% or essentially 100% of the loci listed in Tables I and II.

A cell comprising the same alleles as a cell of line J10102-s69 for at least 75% of the loci listed in Tables I and II is also an embodiment of this invention. In other embodiments, cells comprising the same alleles as a cell of line J10102-s69 for at least 80%, 85%, 90%, 95%, 96%, 97%, 98%, 99% or essentially 100% of the loci listed in Tables I and II, are provided. Also encompassed within the scope of the invention are cultures substantially benefiting from the use of line J10102-s69 in their development, such as hybrid offspring having line J10102-s69 as a parent, and line J10102-s69 having a trait introduced through introgressive matings of offspring back to line J10102-s69, or through transformation. Similarly, an embodiment of this invention is an *Agaricus bisporus* heterokaryon comprising at least one allele per locus that is the same allele as is present in the J10102-s69 line for at least 75% of the marker loci listed in Tables I and II. In other embodiments, heterokaryons comprising at least one allele per locus that is the same allele as is present in the J10102-s69 line for at least 80%, 85%, 90%, 95%, 96%, 97%, 98%, 99% or essentially 100% of the marker loci listed in Tables I and II, are provided. More particularly, the heterokaryon may be a hybrid descendent of line J10102-s69.

Mushroom-forming fungi exhibit an alternation of generations, from heterokaryotic (N+N, with two haploid nuclei, functionally like the 2N diploid state) to homokaryotic (1N) and further upon mating to become heterokaryotic again. In most eukaryotes, a parent is conventionally considered to be either diploid or heterokaryotic. The haploid 'generation' is often, but not always, termed a gamete (e.g., pollen, sperm). In fungi, which are microorganisms, the haploid generation can live and grow indefinitely and independently, for example in laboratory cell culture; while these haploid homokaryons function as gametes in matings, they are equivalent to inbred lines (e.g., of plants) and are more easily referred to as parents (of hybrids). Herein, the term 'parent' refers to the culture that is a, or the, direct progenitor of another culture within the alternating generations of the sexual lifecycle. The term 'line' refers more narrowly to a haploid (N) homoallelic culture within the lifecycle. The N+N heterokaryon resulting from a mating, or comprising a breeding stock, or comprising a culture used to produce a crop of mushrooms, may be called a 'strain'.

If one parental line carries allele 'p' at a particular locus, and the other parental line carries allele 'q', the F1 hybrid resulting from a mating of these two lines will carry both alleles, and the genotype can be represented as 'p/q' (or 'pq', or 'p+q'). Sequence-characterized markers are codominant and both alleles will be evident when an appropriate sequencing protocol is carried out on cellular DNA of the hybrid. The profile of line J10102-s69 can therefore be used to identify hybrids comprising line J10102-s69 as a parent line, since such hybrids will comprise two sets of alleles, one of which sets will be from, and match that of, line J10102-s69. The match can be demonstrated by subtraction of the second allele from the genotype, leaving the J10102-s69 allele evident at every locus. A refinement of this approach is possible with hybrids of *Agaricus bisporus* as a consequence of the heterokaryon (N+N) condition existing in hybrids. The two haploid nuclei can be physically isolated by various known techniques (e.g., protoplasting) into 'neohaplont' subcultures, and each may then be characterized independently. One of the two neohaplont nuclear genotypes from the F1 hybrid will be that of line J10102-s69, demonstrating its use in the mating and its presence in the hybrid.

A heterokaryotic selfed offspring of an F1 hybrid that itself has a IA' genotype will in the example have a genotype of 'p/p', 'q/q', or 'p/q'. Two types of selfing lead to differing expectations about representation of alleles of line J10102-s69 and of the F1 hybrid in the next heterokaryotic generation. When two randomly obtained haploid offspring from the same F1 hybrid, derived from individual spores of different meiotic tetrads, are mated (i.e., in inter-tetrad selfing), representation of the line J10102-s69 marker profile in each recombined haploid parental line and in each sib-mated heterokaryon will be 50% on average, and slightly more than 75% (to about 85%) of heteroallelism present in the F1 hybrid will on average be retained in the sib-mated heterokaryon (the expectation over 75% is due to the mating requirement for heteroallelism at the mating type locus (MAT) on Chromosome 1). Distinctively, in addition, *Agaricus bisporus* regularly undergoes a second, characteristic, spontaneous intra-tetrad form of selfing called intramixis, producing heterokaryotic postmeiotic spores carrying two different recombined haploid nuclei having complementary, heteroallelic MAT alleles. An offspring developing from any one of these spores is a postmeiotic self-mated heterokaryon with ca. 100% retention of the heteroallelism present in the single F1 parent around all 13 pairs of centromeres. In theory this value decreases to an average of 66.7% retention of F1 heteroallelism for distal markers unlinked to their centromeres; however empirical observations suggest higher rates of retention even for such distal markers. Transmission of the line J10102-s69 marker profile in such selfed offspring may be incomplete by a small percentage (typically 0-10%) due to the effects of infrequent meiotic crossovers, while representing 50% on average of the resulting heterokaryotic genome. Both types of selfed offspring are considered to be Essentially Derived Varieties (EDVs) of the initial F1 hybrid, and the latter type comprises most (often 95-100%) of the genotype of the F1, and may express a very similar phenotype to that of the F1 hybrid.

Essentially Derived Varieties are most often derived directly from a single initial culture (e.g., strain); all such derivations produce EDVs. There is no universally accepted definition of an EDV; one example of a definition applicable to plant varieties is provided by the US Plant Variety Protection Act (revised edition, February 2006). The definition employed herein is congruent with the term as it is widely understood. 'Essential derivation' methods of obtaining cultures which are by definition consequently EDVs of a single initial culture of *A. bisporus* include somatic selection, tissue culture selection, single spore germination, multiple spore germination, selfing, repeated mating back to the initial culture, mutagenesis, and transformation, to provide some examples of methods that are well known in the art. Repeated mating back to the initial culture to introgress a single trait into the genetic background of an initial variety or strain is called introgressive trait conversion, and produces an EDV of the initial strain. DNA-mediated transformation of *A. bisporus* has been reported by Velcko, A. J. Jr., Kerrigan, R. W., MacDonald, L. A., Wach, M. P., Schlagnhaufer, C., and Romaine, C. P. 2004, Expression of novel genes in *Agaricus bisporus* using an *Agrobacterium*-mediated transformation technique. Mush. Sci. 16: 591-597, and references therein, herein incorporated by reference. Transformation may introduce a single new gene or allele into the genome of an initial variety.

Therefore, in accordance with the above, one or more embodiments of this invention include a line J10102-s69 progeny mushroom culture, culture part, mushroom, or mushroom part that is a first-generation (F1) heterokaryotic hybrid mushroom culture comprising two sets of alleles, wherein one set of alleles is the same as line J10102-s69 at all of the marker loci listed in Table I. A mushroom cell or hyphal element wherein one set of the alleles is the same as line J10102-s69 at all of the marker loci listed in Table I is also an embodiment of the invention. This mushroom cell or hyphal element may be a part of a culture, a commercial inoculum or 'spawn' product, a mushroom, or a part of a mushroom produced by mating line J10102-s69 with another mushroom culture. Further embodiments of this invention may include an essentially derived variety of the F1 hybrid, produced by inter-tetrad or intra-tetrad selfing of the F1 hybrid, or by modification of the F1 culture, and more specifically by somatic selection, tissue culture selection, single spore germination, multiple spore germination, selfing, repeated mating back to the initial culture, mutagenesis, and transformation.

While many types of molecular markers are known, and can be used, all of these ultimately derive from the primary DNA sequence of the genome. The essential genotype of a line or strain is embodied in its genomic DNA sequence. The marker profile presented in Table I represents selected short segments of the genome sequence of line J10102-s69, at loci which are known to have differing sequences among other lines and strains, selected at widely spaced intervals spanning the entire nuclear genome. Commercial sequencing providers and commercial technologies such as Illumina MiSeq, among others, may be used to obtain whole-genome sequences from total cellular DNA preparations. Other techniques for obtaining genotype profiles may also be used as appropriate.

Line J10102-s69 and its presence in cultures, culture parts, hybrids, mushrooms and mushroom parts can be identified through a molecular marker profile. A mushroom culture cell or hyphal element having the marker profile shown in Table I is an embodiment of the invention. Such a mushroom cell or hyphal element may be heterokaryotic.

Line J10102-s69 represents a new base genetic line into which a new locus or trait may be introgressed. Direct transformation and inbreeding represent two useful methods that can be applied to accomplish such an introgression.

Introgression producing a trait conversion comprises the step of mating line J10102-s69 to a second strain, and then mating progeny of that mating with line J10102-s69, repetitively, until a derived variant of line J10102-s69 incorporating an introduced gene determining a novel trait is obtained. Strains and lines produced by this method may have, for example, in the range of 75, 80, 85, 90, 95, 96, 97, 98, 99, or 99.9% of the DNA of line J10102-s69, and are therefore Essentially Derived Varieties of line J10102-s69, and are an embodiment of the invention.

In order to demonstrate practice of the present invention, the line J10102-s69 was compared to other lines. J10102-s69 is a line selected from among haploid progeny of a 5th generation in a hybrid pedigree initiated by Sylvan America, Inc. in 1993. This line, within a suitable heterokaryotic genetic background, recessively confers a white cap color trait upon heterokaryotic offspring; cap color is determined primarily by recessive alleles at the Ppc-1 locus on Chromosome 8. Line J10102-s69 has the Mat-2 mating type genotype and behavioral phenotype. It also contributes to and supports several commercially desirable traits in hybrid offspring, including crop timing and productivity, and mushroom size, appearance and general retail appeal. Because line J10102-s69 is a haploid line, it is incapable of producing a crop of mushrooms, and consequently no "J10102-s69 mushroom" is obtainable and no direct characterization of a crop or product phenotype is possible. Therefore most selection criteria applied to haploid lines including line J10102-s69 are determined empirically by evaluating a series of matings which share a common parent such as line J10102-s69. In effect, this 'combining ability', i.e., the ability to mate successfully and produce a high proportion of interesting and useful novel hybrids in strain development programs, is applied using qualitative, quantitative, objective and subjective criteria. Line J10102-s69 is among the top-ranked haploid lines discovered from among its cohort of sibling lines. No previous hybrid, prior to creation of hybrids using line J10102-s69, had the particular combination of desirable traits (including specific details of its rounder cap, thicker flesh, and accelerated cropping, plus a particular novel incompatibility phenotype) seen among hybrids incorporating line J10102-s69, as described in Sylvan America, Inc.'s corresponding patent application filed the same day and entitled "Hybrid Mushroom Strain J11500 and Descendants Thereof", herein incorporated by reference. No previous line has ever been observed to produce the combinations of desirable traits observed among hybrids incorporating line J10102-s69.

As previously discussed, the results in Table I compare a specific hybrid mushroom culture strain, namely a strain designated J11500, which has been deposited with the NRRL as Accession No. 50895 and which is the subject of a concurrently filed patent application entitled "Hybrid Mushroom Strain J11500 and Descendants Thereof", the disclosure of which is incorporated by reference, for which line J10102-s69 is a parent with other hybrids. The results show that homokaryotic line J10102-s69 shows good combining ability.

A single mushroom hybrid results from the mating of two haploid, homoallelic lines, each of which has a genotype that complements the genotype of the other. The hybrid progeny of the first generation is designated F1. F1 hybrids may be useful as new commercial varieties for mushroom production, or as starting material for the production of inbred offspring and/or EDVs, or as parents of the next generation of haploid lines for producing subsequent hybrid strains.

Line J10102-s69 may be used to produce hybrid mushroom cultures. One such embodiment is the method of mating homokaryotic line J10102-s69 with another homokaryotic mushroom line, to produce a first generation F1 hybrid culture. The first generation culture, culture part, mushroom, and mushroom part produced by this method is an embodiment of the invention. The first generation F1 culture will comprise a complete set of the alleles of the homokaryotic line J10102-s69. The strain developer can use either strain development records or molecular methods to identify a particular F1 hybrid culture produced using line J10102-s69. Further, the strain developer may also produce F1 hybrids using lines which are transgenic or introgressive trait conversions (narrow modifications') of line J10102-s69. Another embodiment is the method of mating line J10102-s69, or a narrowly modified version of that line, with a different, heterokaryotic culture of *Agaricus bisporus*. This latter method is less efficient than mating using two homokaryotic lines, but can also result in the production of novel hybrid cultures.

The development of a mushroom hybrid in a typical mushroom strain development program involves many or all of the following steps: (1) the obtaining of strains or stocks from various germplasm pools of the mushroom species for initial matings; (2) matings between pairs of pure cultures on sterile microbiological growth media such as potato dextrose agar (PDA); (3) the obtaining and use of promising hybrid strains from matings to produce subsequent generations of homokaryotic progeny lines, such as line J10102-s69, which are individually uniform; (4) the use of those lines in matings with other lines or strains to produce a subsequent hybrid generation; (5) repetition of steps (2-4) as needed; (6) obtaining of pre-commercial hybrid strains and the use of essential derivation techniques such as selfing to produce a final commercial strain. In one embodiment, the repetition of steps (2-4) may be performed up to 5 times. In various other embodiments, steps (2) to (4) may be repeated anywhere from 0 up to 1, 2, 3, 4, 5, 6, 7, 8, 9 or 10 times. The homokaryotic lines are not reproductively competent (fertile). Fertility, the ability to produce a crop of mushrooms, is restored in complementary matings with other haploid, or less commonly, heterokaryotic strains. An important consequence of the homoallelism and homogeneity of the homokaryotic line is that the hybrid between a defined pair of homokaryotic lines may be recreated indefinitely as long as the homokaryotic lines are preserved and/or propagated. In a mating attempt between a homokaryotic line and a heterokaryon, in the absence of somatic recombination, either or both of only two possible defined novel heterokaryotic genotypes may be obtained, each of which will comprise line J10102-s69.

Using line J10102-s69, specific application with repetition of the steps described above can produce any pedigree structure from any arrangement of stocks, lines and hybrids within that structure. A hybrid of the F1, F2, F3, F4, F5, F6, F7, F8, F9, F10 or any subsequent hybrid generation can be produced from line J10102-s69 using steps 1-6 described above.

Although the invention has been described in terms of particular embodiments in this application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

What is claimed is:

1. A culture comprising at least one set of chromosomes of an *Agaricus bisporus* line J10102-s69, the culture of the line J10102-s69 having been deposited under the NRRL Accession Number 50893, wherein said chromosomes comprise all of the alleles of the line J10102-s69 at the sequence-characterized marker loci listed in Table I.

2. The culture of claim 1, wherein said culture is an F1 hybrid *Agaricus bisporus* mushroom culture produced by mating a culture of the line J10102-s69 with a different *Agaricus bisporus* culture.

3. A part of the culture of claim 1 selected from the group consisting of hyphae, mushrooms, spores, cells, and protoplasts.

4. A part of the F1 hybrid mushroom culture of claim 2 selected from the group consisting of hyphae, spores, cells, and protoplasts.

5. A product incorporating the culture of claim 1, the product selected from the group consisting of mycelium, spawn, inoculum, casing inoculum, fresh mushrooms, processed mushrooms, mushroom pieces, and colonized substrates including grain, compost, and friable particulate matter.

6. A product incorporating the F1 hybrid mushroom culture of *Agaricus bisporus* of claim 2, the product selected from the group consisting of mycelium, spawn, inoculum, casing inoculum, fresh mushrooms, processed mushrooms, mushroom pieces, colonized substrates, grain, compost, and friable particulate matter.

7. A mushroom produced by growing a crop of mushrooms from the culture of claim 1.

8. A mushroom produced by growing a crop of mushrooms from the F1 hybrid *Agaricus bisporus* mushroom culture of claim 2.

9. An Essentially Derived Variety of the culture of claim 1, wherein the Essentially Derived Variety is a culture derived from a single initial culture of line J10102-s69, wherein a culture of the line has been deposited under NRRL Accession No. 50893, such that at least 75% of its genome or genotype is present in the genome or genotype of the initial culture of line J10102-s69.

10. An Essentially Derived Variety of the F1 hybrid *Agaricus bisporus* mushroom culture of claim 2, wherein the Essentially Derived Variety is a culture derived from a single initial culture of the F1 hybrid *Agaricus bisporus* mushroom such that at least 75% of its genome or genotype is present in the genome or genotype of the initial culture.

11. A process for introducing a desired trait into a culture of *Agaricus bisporus* line J10102-s69, a culture of the line J10102-s69 having been deposited under NRRL Accession Number 50893, comprising the steps of:
    (1) mating the culture of *Agaricus bisporus* line J10102-s69 to a second culture of *Agaricus bisporus* having the desired trait, to produce a hybrid;
    (2) obtaining an offspring that carries at least one gene that determines the desired trait from the hybrid;
    (3) mating said offspring of the hybrid with the culture of *Agaricus bisporus* line J10102-s69 to produce a new hybrid;
    (4) repeating steps (2) and (3) at least once to produce a subsequent hybrid;
    (5) obtaining a homokaryotic line carrying at least one gene that determines the desired trait and comprising at least 75% of the alleles of line J10102-s69, at sequence-characterized marker loci described in Table I, from the subsequent hybrid of step (4).

12. A process of producing a hybrid mushroom culture, comprising:
    mating a first mushroom culture with a second mushroom culture, wherein at least one of the first and second mushroom cultures is an *Agaricus bisporus* culture having all of the physiological and morphological characteristics of line J10102-s69, wherein the culture of said line J10102-s69 was deposited under the NRRL Accession Number 50893.

13. A hybrid culture produced by the process of claim 12.

14. A part of the hybrid culture of claim 12, selected from the group consisting of hyphae, spores, cells, and protoplasts.

15. A hybrid mushroom produced by growing a crop of mushrooms from said hybrid culture of claim 12.

16. A product incorporating the hybrid culture of claim 12, the product selected from the group consisting of mycelium, spawn, inoculum, casing inoculum, fresh mushrooms, processed mushrooms, mushroom pieces, colonized substrates, grain, compost, and friable particulate matter.

17. An *Agaricus bisporus* culture having all of the physiological and morphological characteristics of line J10102-s69, wherein the culture of said line J10102-s69 was deposited under the NRRL Accession Number 50893.

18. The *Agaricus bisporus* culture of claim 17, further comprising a marker profile in accordance with the marker profile of line J10102-s69 shown in Table I.

19. A cell of the *Agaricus bisporus* culture of claim 17.

20. The cell of claim 19, further comprising a marker profile in accordance with the profile of line J10102-s69 shown in Table I.

21. A spore comprising the cell of claim 19.

22. The *Agaricus bisporus* culture of claim 9 further defined as having a genome comprising a single locus trait conversion.

23. The *Agaricus bisporus* culture of claim 22, wherein the locus confers a trait selected from the group consisting of mushroom size, mushroom shape, mushroom cap roundness, mushroom flesh thickness, mushroom color, mushroom surface texture, mushroom cap smoothness, tissue density, tissue firmness, delayed maturation, basidial spore number greater than two, sporelessness, increased dry matter content increased shelf life, reduced bruising, increased yield, altered distribution of yield over time, decreased spawn to pick interval, resistance to infection by symptoms of or transmission of bacterial, viral or fungal disease or diseases, insect resistance, nematode resistance, ease of crop management, suitability of crop from mechanical harvesting, desired behavioral response to environmental conditions, to stressors, to nutrient substrate composition, to seasonal influences, and to farming practices.

24. A method of producing a mushroom culture comprising the steps of:
    (a) growing a progeny culture produced by mating the culture of claim 17 with a second *Agaricus bisporus* culture;
    (b) mating the progeny culture with itself or a different culture to produce a progeny culture of a subsequent generation;
    (c) growing a progeny culture of a subsequent generation and mating the progeny culture of a subsequent generation with itself or a different culture; and
    (d) repeating steps (b) and (c) for an additional 0-5 generations to produce a mushroom culture.

25. A method for developing a second culture in any generation in a mushroom strain development program comprising:

applying any mushroom strain development technique that results in the development of a second culture, to a first mushroom culture, or parts thereof, wherein said first mushroom culture is selected from the group consisting of (1) a culture comprising at least one set of chromosomes of an *Agaricus bisporus* line J10102-s69, (2) an F1 hybrid *Agaricus bisporus* mushroom culture produced by mating a culture of the line J10102-s69 with a different *Agaricus bisporus* culture, (3) an Essentially Derived Variety culture derived from a single initial culture of line J10102-s69, such that at least 75% of its genome or genotype is present in the genome or genotype of the initial culture of line J10102-s69, (4) an Essentially Derived Variety culture derived from a single initial culture of an F1 hybrid *Agaricus bisporus* mushroom, such that at least 75% of its genome or genotype is present in the genome or genotype of the initial culture of the F1 hybrid *Agaricus bisporus* mushroom, and (5) a culture having all of the physiological and morphological characteristics of line J10102-s69, wherein the culture of said line J10102-s69 was deposited under the NRRL Accession Number 50893, to provide the second culture.

26. The method for developing a mushroom culture in a mushroom strain development program of claim 25 wherein the mushroom strain development technique is selected from the group consisting of inbreeding, outbreeding, selfing, repeated mating back to an initial culture, introgressive trait conversions, essential derivation, pedigree-assisted breeding, marker assisted selection, mutagenesis, and transformation.

27. A method of mushroom strain development comprising the steps of:
   (a) obtaining a molecular marker profile of *Agaricus bisporus* mushroom line J10102-s69, a culture of said line having been deposited under the NRRL Accession Number 50893;
   (b) obtaining an F1 hybrid culture for which the mushroom culture of claim 10 is a parent;
   (c) mating a culture obtained from the F1 hybrid culture with a different mushroom culture and;
   (d) selecting progeny that possess characteristics of said molecular marker profile of line J10102-s69.

* * * * *

UNITED STATES PATENT AND TRADEMARK OFFICE
CERTIFICATE OF CORRECTION

PATENT NO. : 9,648,812 B2
APPLICATION NO. : 14/169578
DATED : May 16, 2017
INVENTOR(S) : Richard W. Kerrigan et al.

Page 1 of 1

It is certified that error appears in the above-identified patent and that said Letters Patent is hereby corrected as shown below:

In the Claims

Column 28, Claim 23, Line 43, "content increased" should read --content, increased--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*